United States Patent

Sandegård

[11] Patent Number: 5,906,585
[45] Date of Patent: May 25, 1999

[54] DEVICE FOR THE TREATMENT OF LEG FRACTURES

[75] Inventor: Jan Sandegård, Odensalagatan 19, S-831 47, Östersund, Sweden

[73] Assignees: Bengt Ingvar Jacobsson; Jan Sandegård, both of Östersund, Sweden

[21] Appl. No.: 08/817,125

[22] PCT Filed: Oct. 3, 1995

[86] PCT No.: PCT/SE95/01123

§ 371 Date: Jun. 27, 1997

§ 102(e) Date: Jun. 27, 1997

[87] PCT Pub. No.: WO96/10970

PCT Pub. Date: Apr. 18, 1996

[30] Foreign Application Priority Data

Oct. 7, 1994 [SE] Sweden .................................. 9403404

[51] Int. Cl.[6] .................................................. A61F 5/00
[52] U.S. Cl. ...................... 602/32; 602/36; 602/5
[58] Field of Search ......................... 602/32, 33, 35, 602/36, 38, 39, 15, 23–25, 5; 606/241, 242

[56] References Cited

U.S. PATENT DOCUMENTS

| 937,354 | 10/1909 | Amos | 602/36 X |
|---|---|---|---|
| 2,007,127 | 7/1935 | Longfellow | 602/35 |
| 4,608,971 | 9/1986 | Borschneck | 602/23 |
| 5,342,288 | 8/1994 | Lee et al. | 602/23 X |
| 5,669,908 | 9/1997 | Gracilla | 602/23 X |

Primary Examiner—Richard J. Apley
Assistant Examiner—Denise Pothier
Attorney, Agent, or Firm—John Lezdey & Assoc

[57] ABSTRACT

The invention relates to a traction device for treating leg fractures 81, wherein the device 1 includes a traction bar 2 or the like which carries at its rear end a branched support 3 intended for abutment with the crotch region of a patient or a person on which the device is used, and which carries at its front end at least one attachment point 4 for the attachment of tensioning devices 5 which are intended to act between the attachment point or attachment points and the feet or lower leg parts of said person. The branched support 3 includes support surfaces 35, 36 which are positioned for supportive engagement with the ischial tuberosities (tuber ossis ischii) 80 of said person. The branched support 3 includes a recess 34 or opening which provides room for the genital organs of said person. The branched support 3 includes a base part 30 which includes a part 31 by means of which the branched support can be affixed to the traction bar 2. The traction bar 2 can be adjusted to different lengths, so as to adjust the distance between the branched support 3 and the tensioning-device attachment point or points 4 in relation to said person.

6 Claims, 1 Drawing Sheet

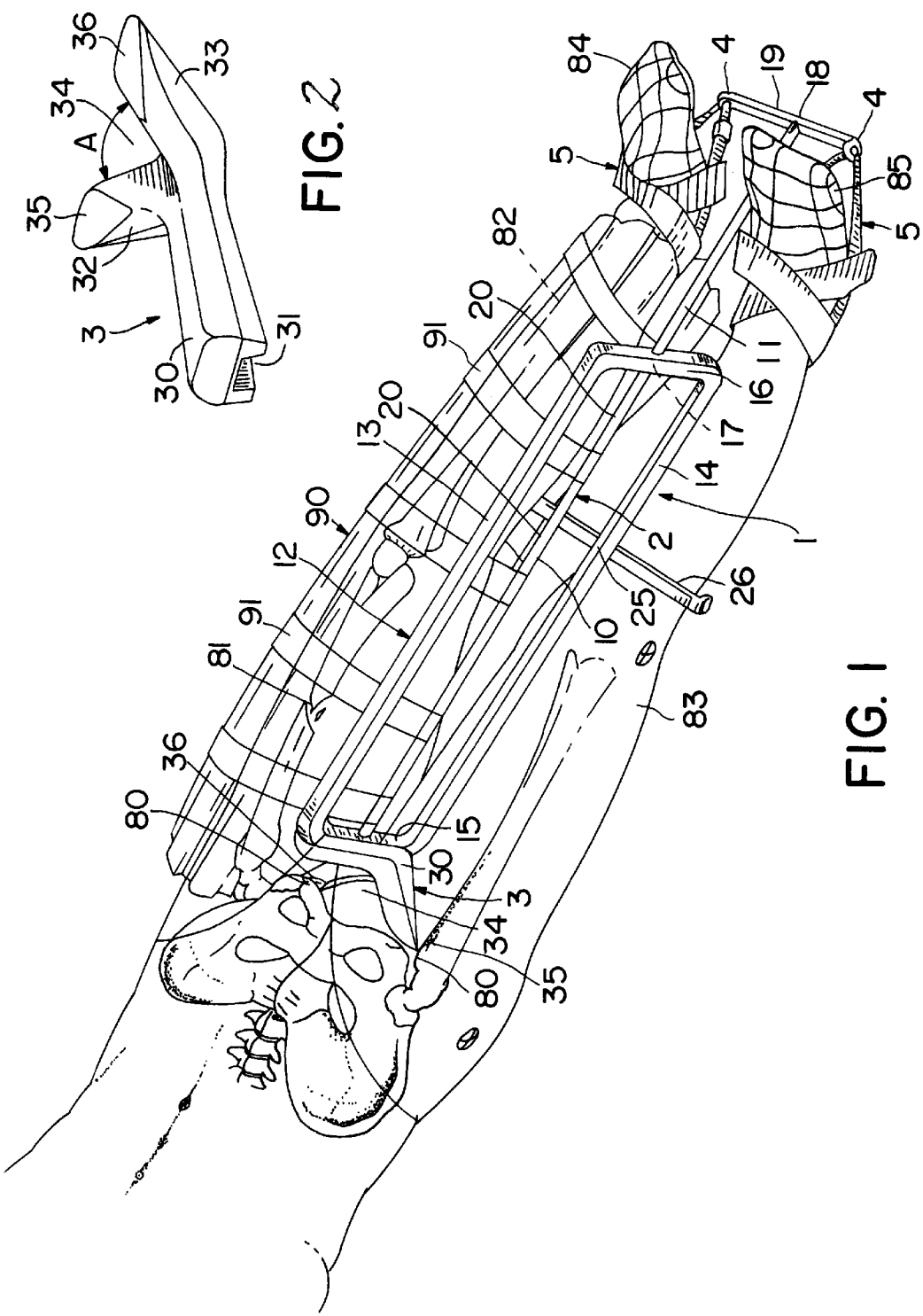

DEVICE FOR THE TREATMENT OF LEG FRACTURES

BACKGROUND OF THE INVENTION

1. Field of the Invention

The present invention relates to a device for applying traction to a fractured leg. The invention also relates to a method of using the device.

2. Description of the Prior Art

When administering first-aid to a person who has suffered a fractured or broken leg, such as a fractures femur and/or a lower part of the leg, immediately on the site of the accident, an attempt is normally made to straighten and reset the fractured bone then apply a splint in order to hold the fractured bone in place prior to transporting the injured person to hospital for further treatment.

In the case of a fracture to the lower leg, it often suffices to fixate the broken bone with the aid of splints or some corresponding means. However, fractures to the lower leg and the majority of femur fractures require the leg to be stretched by applying an appropriate stretching or traction force to the leg at the same time as the splint is being applied to hold the fracture fixated. So-called traction bars or stretchers are used in such cases.

Such traction devices enable tension to be applied on affected parts of the leg in its longitudinal direction. Traction can be applied to the leg with the aid of a so-called traction device/traction bar through the medium of a counter-pressure means/support device which is provided at the rear/other end of the device and which lies supportively against the pelvis of the injured person, and also through the medium of an attachment means which is located on the front end/the first end of the device and which acts relative to the foot part of the injured person. It has been found that the traction force required to apply traction to the leg of an injured person in hospital without causing pain to the patient is about 7–10% of the body weight of the person/patient, i.e. a force of about 5–10 kp. The supportive part of the body (the pelvis) and the device attachment part (the foot part) are subject to equal forces when stretching the leg. The fractured bone is extended by traction forces that are applied via the foot of the injured person and the counter-pressure forces acting on his/her pelvis. However, it has been found very difficult to obtain a device-supporting point with which no unpleasantness is inflicted in the form of physical pain and numbness.

The majority of traction devices that are available commercially are constructed for treating only one broken leg at a time. A traction device which is constructed for use with both legs simultaneously will enable both legs to be streched simultaneously and therewith distribute symmetrically on load the body of the patient. Such as device will also find use when both legs are fractured.

Such devices primarily use the pubic bone (crotch) and the ischial tuberosity as their supporting points. Pressure against the pubic bone is liable to cause discomfort, due to squeezing of the external genital organs.

The object of the present invention is to provide an attractive device for optimal traction of a fractured leg while minimizing discomfort and numbness at the same time. This object is achieved with the inventive traction device having the characteristic features set forth herein.

The inventive traction device affords the following advantages, among others:

SUMMARY OF THE INVENTION

The present invention teaches a device for applying traction to a fracture of at least one leg of a patient. The device comprises: a traction bar having a rear end and a front end. A branched support is fixedly attached to the rear end for abutment with a crotch region of the patient. At least one attachment point located at the front end. Tensioning devices are connected to the attachment point for acting between the attachment point and the leg of said patient. The branched support includes support surfaces for supportive abutment with ischial tuberosities of the patient and a recess or an opening in which genital organs of the patient can lie.

Because of the inventive configuration of the device-supporting means/the branched support, there is obtained a symmetrical and particularly well-balanced force distribution which is technically beneficial and lenient to the patient concerned.

The branched support is configured anatomically and utilizes both of the patient's ischial tuberosities (tuber ossis ischii) as counter-pressure points/supportive points. Thus, the traction or stretching force required to treat a bone fracture will be distributed over two support points or support surfaces. The requisite pressure is thus distributed over two support points, wherein each support point need take-up only half the pressure, while the active abutment surfaces of the support device/branched support are adapted anatomically to the configuration of the ischial tuberosities.

The branched support has a generally cup-shaped recess which eliminates pressure against the external genitals. There will thus be no pressure that produces numbness.

The inventive device thus uses the ischial tuberosities (tuber ossis ischii) of the patient as a counter-pressure support instead of the patient's pubic bone, which is often considered unpleasant due to the pressure thus exerted on the genitals of the patient.

The inventive device can be adapted readily to the body size/leg length of the person being treated. One and the same device can be used with both children and adults.

The inventive device can be used in the treatment of femur fractures and/or lower leg fractures on both legs, even when both legs are fractured at the same time.

The inventive device provides room for the injured part of the leg to swell, is reliable in use, and enables the patient to be lifted comfortably and will allow X-rays to pass through. The inventive device also provides room for auxiliary splint devices, such as reinforced pads, for instance.

The invention affords both technical and economical advantages.

BRIEF DESCRIPTION OF THE DRAWINGS

The invention will now be described in more detail with reference to exemplifying embodiments thereof and also with reference to the accompanying drawing, in which FIG. 1 is an X-ray view in perspective of the inventive device used on a patient; and FIG. 2 is a perspective view of the device support means/branched support.

DESCRIPTION OF THE PREFERRED EMBODIMENT

The inventive device 1 includes a so-called traction bar 2 which has at its rear end a support means/counter-pressure means in the form of a branched support 3, and is provided at its front end with attachment points 4 for the attachment of tensioning devices 5.

The traction bar 2 can be adjusted to different lengths, for adjustment of the distance between the branched support 3 and the attachment points 4. The illustrated traction bar 2 includes two telescopic tubes 10, 11, wherein the outer telescopic tube 10 carries a frame 12 and the branched support 3. The frame 12 of the illustrated embodiment is elongated and of rectangular cross-section and includes an upper long-side part 13, a lower long-side part 14, a rear short-side part 15 and a front short-side part 16. The outer tube 10 of the illustrated embodiment has a round cross-section and extends between the short-side 15 and 16 of the frame, and is connected to said short-side.

The other telescopic tube 11 of the illustrated embodiment has a round cross-section and extends into the outer tube 10 through a hole 17 in the short-side 16 of the frame, for telescopic coaction with the outer tube 10. The outer tube 10 and the inner tube 11 are thus mutually of a shape and size which will enable the tube to telescope in relation to one another. The front end 18 of the inner tube 11 carries an anchoring means in the form of a fastening stirrup 19 which has attachment points 4 for the attachment of two tensioning straps or ankle straps 5, or like tensioning devices.

The traction bar 2 comprised of the telescopic tubes 10 and 11 can be adjusted to different lengths, so as to enable the length of the device 1 to be adapted to the leg length of the patient concerned. This adjustment to the length of the traction device 1 can be achieved, for instance, by providing the outer tube 10 with a number of holes 20 and by providing the inner tube 11 with a spring-biassed ball (not shown) capable of entering a selected hole 20 so as to lock the outer and inner tube together. It will be understood that the spring-loaded ball may be replaced with a locking pin or some like device if so desired.

The frame 12 carries a bottom support bar 26 which is preferably pivotal about a pivot point 25 and which can be swung-in to an inactive position in which it is located beneath the frame part 14, and swung-out to a use position in which the bar extends transversely to the frame part 14, as illustrated in FIG. 1.

The traction bar 2 carries at its rear end an inventive support means in the form of a branched support 3. The branched support 3 includes a base part 30 that has a longitudinally extending groove or channel 31. The shape and size of the groove 31 coincides with the shape and size of the short-side 15 of the frame, wherein the branched support 3 can be affixed to the frame 12 by gluing or screwing the same thereto for instance. If desired, the cross-sectional size of the groove 31 may be smaller than the cross-sectional size of the frame part 15, so that the branched support 3 can be pressed-fitted to the frame part 15.

The branched support 3 has two obliquely and outwardly projecting legs 32 and 33 which define therebetween an angle A of about 90°, thereby presenting a recess 34 in the V-form defined by the legs 32 and 33. The leg 32 is terminated with an abutment surface 35 and the leg 33 is terminated with an abutment surface 36. The angle at which the abutment surfaces 35 and 36 are inclined and the size of said abutment surfaces are adapted for effective coaction with the ischial tuberosities (tuber ossis ischii) 80 of both small and large people. FIG. 1 illustrates schematically this coaction of the branched support means with the ischial tuberosities 80. The base part 30 of the branched support extends generally at right angles to the common plane of the legs of the V at the branching point of the legs.

When treating on-site a person suffering from a femur fracture 81, the inventive traction device 1 is used and functions in the following manner:

The traction device 1 is placed between the patient's legs 82 and 83, so that the abutment surfaces 35 and 36 seat against the ischial tuberosities 80. The bottom support 26 is extends to its use position (FIG. 1) and the length of the traction bar 2 is adjusted to the length of the patient's legs. The patient's feet 84 and 85 are then anchored by means of the tension straps 5 attached to the attachment points 4 on the attachment stirrup 19, whereafter the straps are tightened until the desired traction force has been reached in both legs 82 and 83, so as to obtain desired traction over the fracture 81.

The fractured bone, or bones, of the patient can be set with the aid of a reinforced splint-pad 90 which may be applied with the aid of fastener straps 91, which can also be anchored on the device 1, as illustrated in FIG. 1. When needing to move the patient, the lower part of the patient's body can be lifted by grasping the upper part 13 of the frame with the patient's legs resting on the bottom support 26. The patient can then be transported to a hospital, for instance.

By subjecting both legs 82, 83 to traction by means of the foot straps/tension straps 5, both ischial tuberosities 80 will share the reaction forces that are generated thereby, with the genital organs of the patient being located in the recess 34 of the branched support 3 and therewith protected from unpleasant pressures. Any subsequent adjustment needed to the traction force can be readily effected.

It will be understood that the inventive device 1 can also be used effectively to treat double lower-leg fractures and/or femur fractures, wherewith the application of splints to the fractured region and the stretching of said regions are adapted to suit prevailing circumstances, wherewith it may be needed to use several reinforced splint-pads, for instance.

In one simple embodiment of the invention, the inventive device need only comprise one single traction bar 2 which need not necessarily be telescopic, wherein the rear end of the traction bar will carry an inventive branched support 3 whose base part 30 is adapted for attachment to the traction bar, and wherein the traction bar will carry at its front end one or more attachment points 4 for the attachment of tensioning straps 5 for coaction with the patient's feet or lower leg.

As will be understood, the traction bar 2 may be constructed in many different way and need not be telescopic, but may be made adjustable with regard to its length in some other way. For instance, instead of using a length-adjustable traction bar, several different attachment points, or movable attachment points, can be provided for the tensioning devices 5. The design of the attachment stirrup 19 can be modified to enable one single attachment point to be used, for instance. The frame 12 and the bottom support 26 may be excluded or given another design.

It will also be understood that the branched support 3 may also be modified while retaining the abutment surfaces 35, 36 and the recess 34 defined by the legs 32, 33. The abutment surfaces 35 and 36 may be flat or slightly curved. The base part 30 may also be designed differently to the illustrated base part.

The branched support 3 may be made of a plastic material and remaining parts of the device 1 from metal for instance, although it will be understood that the branched support and traction device may be made of any suitable material.

The tensioning devices 5 may be made of a plastic material or textile material and include suitable tensioning elements and/or so-called touch-and-close devices, such as Velcro® fasteners.

As will be understood, an undamaged leg need not be subjected to traction forces of the same magnitude as a fractured leg when using the inventive device.

It will also be understood that the telescopic tube arrangement may have a built-in spring-action which facilitates subsequent tightening of the tension straps.

It will therefore be understood that the invention is not restricted to the illustrated and described exemplifying embodiments thereof and that changes and modifications can be made within the scope of the following claims.

I claim:

1. A device for applying traction to a leg fracture, wherein the device includes a traction bar having at its rear end a branched support for abutment with the crotch region of a patient or a person on which the device is used, and having at its front end at least one attachment point for the attachment of tensioning-devices to act between the at least one attachment point and the feet or lower leg parts of the patient or person, and wherein the branched support includes first and second support surfaces, the first support surface is configured for supportive abutment with one ischial tuberosity of the person and the second support surface is configured for supportive abutment with the other tuberosity of the person; and wherein the branched support includes a recess or an opening configured to provide room for the genital organs of the person.

2. A device for applying traction to a fracture of at least one leg of a patient; said device comprising:

a traction bar having a rear end and a front end;

a branched support fixedly attached to said rear end configured to abut a crotch region of the patient;

at least one attachment point located at said front end;

tensioning devices connected to said attachment point for acting between said attachment point and the leg of the patient;

wherein said branched support includes first and second support surfaces, the first support surface is configured for supportive abutment with one ischial tuberosity of the patient and the second support surface is configured for supportive abutment with the other ischial tuberosity of the patient and a recess or an opening configured to provide room for genital organs of the patient.

3. A device according to claim 2, wherein said support surfaces comprise end surfaces and at least two V-forming legs extending out from a base part.

4. A device according to claim 3, wherein said base part has a longitudinally extending groove or channel for fixedly attaching said branched support to said traction bar.

5. A device according to claim 3, wherein said traction bar is adjustable to accommodate different distances between said branched support and said attachment point.

6. A device according to claim 3, wherein said traction bar includes at least two mutually telescopic tubes, and wherein one of said tubes carries said branched support and said other tube carries said attachment point.

* * * * *